United States Patent
Majeed et al.

(10) Patent No.: US 8,394,852 B2
(45) Date of Patent: Mar. 12, 2013

(54) INOTILONE DERIVATIVES AS COHERENT BIOLOGICAL RESPONSE MODIFIER (CBMR)

(75) Inventors: Muhammed Majeed, East Windsor, NJ (US); Kalyanam Nagabhushanam, East Windsor, NJ (US); Samuel Manoharan Thomas, Bangalore (IN); Subbalakshmi Prakash, East Windsor, NJ (US)

(73) Assignee: Sami Labs Ltd, Bangalore (IN)

( * ) Notice: Subject to any disclaimer, the term of this patent is extended or adjusted under 35 U.S.C. 154(b) by 256 days.

(21) Appl. No.: 12/872,675

(22) Filed: Aug. 31, 2010

(65) Prior Publication Data

US 2011/0054018 A1    Mar. 3, 2011

Related U.S. Application Data

(60) Provisional application No. 61/238,533, filed on Aug. 31, 2009.

(51) Int. Cl.
   *A61K 31/34* (2006.01)

(52) U.S. Cl. .................. 514/461; 514/473; 514/731
(58) Field of Classification Search .................. 514/461, 514/473, 731
   See application file for complete search history.

(56) References Cited

PUBLICATIONS

Shamshina et al., Tetrahedron Letters, 48, 2007, 3767-3769.*
Wangun et al., Org.Biomol.Chem, 2006, 2545-2548.*
Remington the Science and Practice of Pharmacy, 19th Edition, pp. 710-712; pp. 1614-1617; pp. 1515-1519: 1995.*

* cited by examiner

*Primary Examiner* — Renee Claytor
*Assistant Examiner* — Shobha Kantamneni

(57) ABSTRACT

Optimal compositions of derivatives of 5-methyl-3(2H)-furanone compounds and phenylpropanoid polyketides related to inotilone, that exert biological response modification in health and disease, and their method of preparation, are disclosed. Methods of treating degenerative conditions stemming from over-expression of inducible nitric oxide synthase (iNOS) using these compositions are also disclosed.

3 Claims, No Drawings

INOTILONE DERIVATIVES AS COHERENT BIOLOGICAL RESPONSE MODIFIER (CBMR)

CROSS-REFERENCE TO RELATED APPLICATIONS

This application claims the benefit of provisional U.S. patent application No. 61/238,533 filed on Aug. 31, 2009, the contents of which are incorporated herein by reference.

FIELD OF THE INVENTION

The invention discloses optimal compositions of derivatives of 5-methyl-3(2H)-furanone compounds and phenylpropanoid polyketides related to inotilone, that exert biological response modification in health and disease, and their method of preparation.

BACKGROUND OF THE INVENTION

There is need for nutrition-derived disease prevention and disease treatment support which would intelligently and predictably modify host response against inappropriate or inadequate reaction of the body to an existing or a potential disease. This is a novel category in disease prevention and treatment. This category is different from the concept of enhancing prevention or treatment focused on modification of the prevention/intervention modalities, e.g. modification of vaccine or a drug. This approach is also different from disease prevention based on, e.g. good nutrition or physical exercise which provides general support to the organism. The proposed novel category would include compounds to intelligently repair host mechanisms that may trigger disease or aggravate the existing disease. Inotilone, a natural compound derived from *Inonotus* sp edible fungi, exemplifies the new prevention/treatment category described here as coherent biological response modifier (cBMR).

Inotilone, 5-methyl-3(2H)-furanone derivative, and related phenylpropanoid polyketides from *Inonotus* sp. have been previously shown to be potent anti-inflammatory agents and inhibitors of cyclooxygenase and xanthone oxidase enzymes (Wangun H V, et al. Org Biomol Chem. 2006 Jul. 7; 4(13): 2545-8); modulate immunological and inflammatory responses (Pan, M H et al, J. Agric. Food Chem 2009, 57(11): 4467-4477; Lull, C et al. Mediators. Inflamm. 2005, 2005(2): 63-80); show antihyperglycemic and antilipidperoxidative effects (Sun, J E et al., J. Ethnopharmacology, 118(1):7-13, 2008); and antitumor effects (Youn, M J et al., World J Gastroenterol. 14(4): 511-517, 2008; Kahlos, K et al. Planta Medica, 52(6):554).

Inotilone blocked protein and mRNA expression of iNOS but not COX-2. Instead, inotilone inhibited prostaglandin E(2) production through decreasing the enzyme activity of COX-2. The repression of iNOS but not COX-2 expression may come from the differential effect of inotilone on nuclear factor-kappaB (NFkappaB) and CCAAT/enhancer-binding protein beta Treatment with inotilone resulted in the reduction of LPS-induced nuclear translocation of NFkappaB subunit and the NFkappaB-dependent transcriptional activity by blocking phosphorylation of inhibitor kappaB (IkappaB) alpha and p65 and subsequent degradation of inhibitor kappaBalpha. Inotilone also inhibited LPS-induced activation of PI3K/Akt and extracellular signal-regulated kinase 1/2 and p38 mitogen-activated protein kinase. (Kuo, Y C et al, Mol Nutr Food Res. 53(11):1386-95, 2009).

SUMMARY OF THE INVENTION

Inotilone, an unusual 5-methyl-3(2H)-furanone derivative, extracted from the *Inonotus* species have been previously shown to be a potent inhibitor of inflammation. The invention describes analogues of inotilone, and methods and compositions thereof.

DESCRIPTION OF THE INVENTION

Inotilone has the following structure.

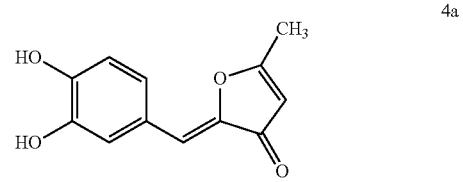 [SMILES: CC1=CC(=O)/C(=C/c2ccc(O)c(O)c2)O1]

4a

Inotilone Analogues

The analogues were created keeping in mind that the acidity of the phenolic group may play a key role in controlling the biological activity of the core structure.

The acidity of the phenolic groups can be enhanced by substitution on the ortho positions by intramolecular hydrogen bonding groups such as methoxy group as exemplified by compound 4(c); Alternatively other compounds can be envisaged such as o-nitro, cyano, sulfonic acids, —COOR groups (where R=alkyl, aryl, cyclic). Also one can envisage hydrogen bonding heterocyclics such as 2-pyridyl, 2-imidazoloyl etc.

The acidity can also be modulated down by substitution of the ortho positions (either one ortho position or both the ortho positions). Thus compound 4 (e) was designed wherein the phenolic group is flanked on both sides by bulky and nonpolar t-butyl groups which will lower the acidity of the phenolic group.

Also one can visualize compounds such as 5 which can in vivo can give rise to 4(e) by elimination of 5-methyl-furan-3-one moiety.

The compounds synthesized are only exemplary designed to illustrate the concept of influencing the acidity of the phenolic group by proper substitution.

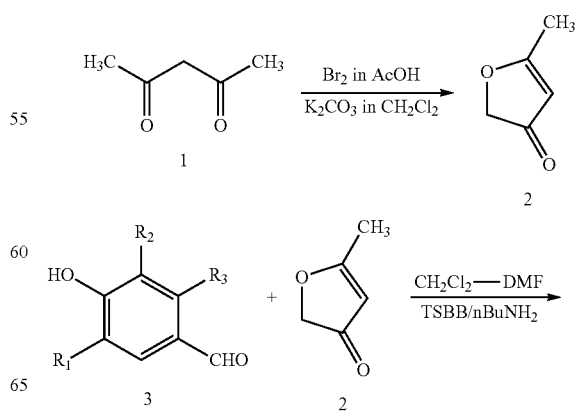

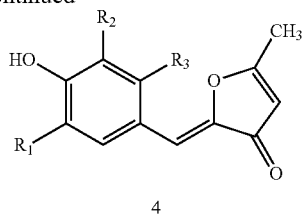

3a & 4a: R₁ = OH R₂ = H R₃ = H
3b & 4b: R₁ = OCH₃ R₂ = H R₃ = H
3c & 4c: R₁ = OCH₃ R₂ = OCH₃ R₃ = H
3d & 4d: R₁ = H R₂ = H R₃ = OH
3e & 4e: R₁ = —C(CH₃)₃ R₂ = C(CH₃)₃ R₃ = H

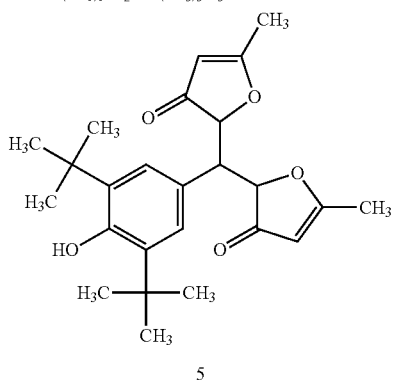

Procedure for the Preparation of Inotilone and its Analogues

Example I

5-Methyl-furan-3-one 9 (2)

Acetylacetone (1) (200 g, 2.0 mol) was taken in a 2 L three necked round bottomed flask fitted with an addition funnel, a mechanical stirrer and the system protected from moisture using calcium chloride guard tube. Glacial acetic acid (600 mL) was added with stirring. Bromine (80 mL, 1.6 mol) was dropped in over a period of 45 min. at room temp. with stirring The color of the reaction mixture became pale yellow. This was stirred for 20 min. Water (500 mL) and dichloromethane (400 mL) were added and stirred for 10 min. The dichloromethane layer was separated, washed with water (3×500 mL), dried over anhy. sodium sulfate (200 g), filtered, and the filtrate contains about 108 g of crude bromoacetylacetone.

Dichloromethane (1.2 L) and anhydrous potassium carbonate were taken in a 3 L three necked round bottomed flask fitted with a condenser, an addition funnel, mechanical agitator and a guard tube. The crude bromoacetylacetone in dichloromethane was taken in the addition funnel and added to the slurry of potassium carbonate in dichloromethane with vigorous stirring over a period of 20 min. This is exothermic and dichloromethane refluxes. The reaction mixture is stirred for a further period of 20 min. The reaction mixture is filtered, filtrate concentrated under reduced pressure in a rotary evaporator. The residual liquid is distilled under vacuum to get 5-methyl-furan-3-one (2) as a colorless liquid (18.0 g, 30% yield) at 43-48° C./5 mm.

$^1$H NMR (CDCl₃, 300 MHz): δ 2.265 (q, J=0.9 Hz, 3H), 4.512 (q, J=0.9 Hz, 2H), 5.497 (q, 0.9 Hz, 1H).

$^{13}$C NMR (CDCl₃, 75 MHz): δ 16.795, 75.542, 104.858, 191.872, 202.993

GC-MS: m/z 98 (M⁺)

Example II

Inotilone (4a)

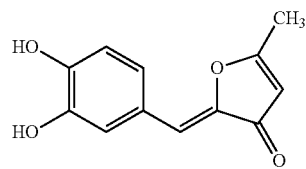

5-methyl-furan-3-one (2, 5.8 g, 0.059 mol) was dissolved in dichloromethane (80 mL) taken in a 250 mL three necked round bottomed flask under dry conditions. 3,4-Dihydroxybenzaldehyde (3a, 7.34 g, 0.0531 mol) was added with stirring. This resulted in a slurry, and addition of DMF (5.8 mL) resulted in a homogenous solution. This mixture was cooled to 0-5° C. in an ice-bath. Tri-sec-butyl borate (TSBB, 13.5 g, 0.059 mol) was added with stirring. A red color developed. This was allowed to warm to room temp. on its own with stirring, and stirred over night. The reaction mixture was poured into acetic acid (5% aq. solution, 120 mL) pre-heated to 60° C., and stirred for 30 min. The organic layer was separated, and the aq. phase extracted with ethyl acetate (2×60 mL). The organic extracts combined, dried over anhy. sodium sulfate (50 g), filtered and the solvents stripped off under vacuum to get a brown thick liquid (20 g). This was chromatographed on a silica gel column (39×3.1 cm) using 10% ethyl acetate in hexane to ethyl acetate to get the pure inotilone (4a) as an yellow powder (2.5 g, 20% yield), m.p. 208.8-210.4° C.

$^1$H NMR (DMSO-d₆, 300 MHz): δ 2.403 (d, J=0.9 Hz, 3H), 5.842 (br q, 1H), 6.512 (s, 1H), 6.815 (d, J=8.4 Hz, 1H), 7.180 (dd, J=8.4 Hz, 2.1 Hz, 1H), 7.363 (d, J=2.1 Hz, 1H), 9.273 (s, 1H, —OH), 9.700 (s, 1H, —OH).

$^{13}$C NMR (DMSO-d₆, 75 MHz): δ 15.658, 105.436, 111.902, 115.860, 117.906, 122.891, 124.716, 144.303, 145.447, 148.130, 180.465, 186.630.

LC-MS: m/z 219 (M⁺+1)

Elemental Analysis: C, 65.75% (requires 66.05%) and H, 4.72% (requires 4.62%).

Example III

2-(4-Hydroxy-3-methoxy-benzylidene)-5-methyl-furan-3-one (4b)

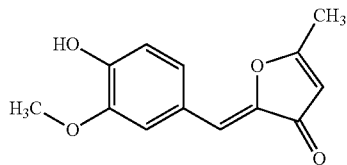

5-methyl-furan-3-one (2, 7.0 g g, 0.071 mol) was dissolved in dichloromethane (40 mL) and taken in a 3-necked 500 mL round bottomed flask fitted with a mechanical agitator and calcium chloride guard tube. Vanillin (3b, 9.0 g, 0.059 mol) dissolved in dichloromethane (40 mL) was added. The mixture was cooled to 0-5° C. with stirring. Tri-sec-butyl borate (15.0 g, 0.065 mol) was added and stirred for 2 h. The color of the reaction mixture turned yellow. n-Butyl amine (2 drops) was added and the reaction mixture allowed to warm to room temp. on its own and stirred at room temp. overnight. The yellow color of the reaction mixture intensified. This mixture was poured into 5% aq. acetic acid solution (120 mL) preheated to 60° C. with stirring. This was stirred for 30 min., and then allowed to settle down. The dichloromethane layer was isolated and concentrated under reduced pressure to get a red color thick liquid. Hexane (80 mL) was added to this gummy material and stirred overnight. A yellow color solid crystallized out. This was filtered, dried in vacuo at 110° C. to get pure 2-(4-hydroxy-3-methoxy-benzylidene)-5-methyl-furan-3-one (4b, 10.0 g, 61% yield) as pale yellow powder, m.p. 167.5°-170.0° C.

$^1$H NMR (CDCl$_3$, 300 MHz): δ 2.399 (d, J=0.9 Hz, 3H), 3.941 (s, 3H), 5.723 (br q, 1H), 6.163 (s, 1H, —OH), 6.659 (s, 1H), 6.968 (d, J=8.1 Hz), 1H), 7.339-7.385 (m, 2H).

$^{13}$C NMR (CDCl$_3$, 75 MHz): δ 16.164, 55.896, 106.170, 112.914, 113.273, 114.989, 124.467, 126.417, 145.396, 146.686, 147.808, 180.004, 188.200.

MS: m/e 233 (M$^+$+1).

Example IV 2-(4-Hydroxy-3,5-dimethoxy-benzylidene)-5-methyl-furan-3-one (4c)

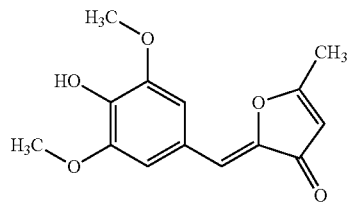

4c 5-methyl-furan-3-one (2, 6.0 g g, 0.061 mol) was dissolved in dichloromethane (40 mL) and taken in a 3-necked 250 mL round bottomed flask fitted with a mechanical agitator and calcium chloride guard tube. Syringaldehyde (3c, 13.3 g, 0.073 mol) dissolved in dichloromethane (40 mL) was added. The mixture was cooled to 0-5° C. with stirring. Tri-sec-butyl borate (14.0 g, 0.061 mol) was added and stirred for 2 h. n-Butyl amine (4 drops) was added, the reaction mixture allowed to warm to room temp. on its own with stirring and stirred at room temp. overnight. The orange yellow color reaction mixture was poured into 5% aq. acetic acid solution (120 mL) preheated to 60° C. with stirring. This was stirred for 30 min., and then allowed to settle down. The dichloromethane layer was isolated and concentrated under reduced pressure to get an orange yellow color thick liquid. Water (20 mL), followed by ethyl acetate (100 mL) were added to this thick gummy material and the mixture concentrated under reduced pressure in a rotary evaporator until the product crystallized out. This was filtered, dried in vacuo at 110° C. to get pure 2-(4-Hydroxy-3,5-dimethoxy-benzylidene)-5-methyl-furan-3-one (4c) (7.0 g, 44% yield) as an orange yellow powder, m.p. 187.9-189.6° C.

$^1$H NMR (CDCl$_3$, 300 MHz): δ 2.405 (d, J=0.9 Hz, 3H), 3.939 (s, 3H), 5.730 (br q, 1H), 5.939 (s, 1H), 6.627 (s, 1H), 7.082 (s, 2H).

$^{13}$C NMR (CDCl$_3$, 75 MHz): δ 16.127, 56.262, 106.140, 108.530, 112.928, 123.367, 137.024, 145.476, 147.089, 179.923, 188.053.

MS: m/e 263 (M$^+$+1).

Elemental analysis: Found: C, 63.88%; H, 5.35%; requires C, 64.11%; H, 5.38%.

Example V 2-(2,4-Dihydroxy-benzylidene)-5-methyl-furan-3-one (4d)

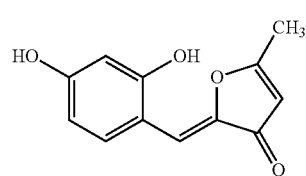

4d 5-methyl-furan-3-one (2, 5.9 g g, 0.060 mol) was dissolved in dichloromethane (80 mL) and taken in a 3-necked 500 mL round bottomed flask fitted with a mechanical agitator and calcium chloride guard tube. 2,4-Dihydroxybenzaldehyde (3d, 7.4 g, 0.053 mol) dissolved in dimethylformamide (8 mL) was added. The mixture was cooled to 0-5° C. with stirring. Tri-sec-butyl borate (13.4 g, 0.058 mol) was added and stirred for 2 h. n-Butyl amine (9 drops) was added over a period of 3 h and the reaction mixture allowed to warm to room temp. on its own and stirred at room temp. overnight. The dark red color solution was poured into 5% aq. acetic acid solution (120 mL) preheated to 60° C. with stirring. This was stirred for 30 min., and then allowed to settle down. The dichloromethane layer was isolated and concentrated under reduced pressure to get red color gummy material. This gummy material was washed with water (3×20 mL). Acetonitrile (20 mL) was added to the gummy material and stirred vigorously. The product precipitated out. This was filtered, washed with acetonitrile (20 mL), and the filtered solid dried in vacuo at 110° C., get pure 2-(2,4-Dihydroxy-benzylidene)-5-methyl-furan-3-one (4d) as a red powder (6.5 g, 50% yield), m.p. 239.4-242.5° C. (decomposes).

$^1$H NMR (DMSO-d$_6$, 300 MHz): δ 2.383 (d, J=0.9 Hz, 3H), 5.813 (br q, 1H), 6.363-6.410 (m, 2H), 6.942 (s, 1H), 7.834 (d, J=8.4 Hz, 1H), 10.167 (br s, 2H, —OH).

$^{13}$C NMR (DMSO-d$_6$, 75 MHz): δ 15.731, 102.276, 105.604, 105.978, 108.405, 110.157, 132.522, 144.017, 159.455, 161.126, 179.922, 186.600.

MS: m/e 219 (M$^+$+1).

Example VI 2-(3,5-Di-tert-butyl-4-hydroxy-benzylidene)-5-methyl-furan-3-one (4e) and 2-[Bis-(3-keto-5-methyl-furanyl)]-3,5-di-tert-butyl-4-hydroxyphenylmethane (5)

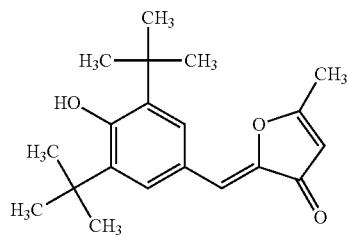

4

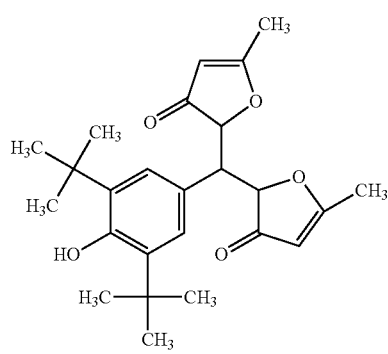

5

5-methyl-furan-3-one (2, 5.0 g g, 0.051 mol) was dissolved in dichloromethane (50 mL) and taken in a 3-necked 500 mL round bottomed flask fitted with a mechanical agitator and calcium chloride guard tube. 3,5-di-tert-butyl-4-hydroxybenzaldehyde hemihydrate (3e, 12.0 g, 0.049 mol) dissolved in dichloromethane (100 mL) was added. The mixture was cooled to 0-5° C. with stirring. Tri-sec-butyl borate (11.7 g, 0.051 mol) was added and stirred for 2 h. n-Butyl amine (6 drops) was added and the reaction mixture allowed to warm to room temp. on its own with stirring and stirred at room temp. overnight. The dark yellow color solution was poured into 5% aq. acetic acid solution (120 mL) preheated to 60° C. with stirring. This was stirred for 30 min., and then allowed to settle down. The dichloromethane layer was isolated and concentrated under reduced pressure to get yellow color solid. This was chromatographed on silica gel column (36×4 cm) using 10% ethyl acetate in hexane as eluent. A yellow color solid (0.5 g, $R_f$ 0.94 on silica gel TLC in 60% ethyl acetate in hexane) was isolated and characterized as 2-(3,5-di-tert-butyl-4-hydroxybenzylidene)-5-methyl-furan-3-one (4e), m.p. 155.1-157.5° C.;

$^1$H NMR (CDCl$_3$, 300 MHz): δ 1.465 (s, 18H), 2.384 (d, J=0.9 Hz, 3H), 5.597 (s, 1H, —OH), 5.711 (br q, 1H), 6.699 (s, 1H), 7.683 (s, 2H).

$^{13}$C NMR (CDCl$_3$, 75 MHz): δ 16.054, 30.092, 34.337, 106.097, 113.904, 123.463, 129.174, 136.424, 145.286, 155.923, 179.660, 188.244.

MS: m/e 315 (M$^+$+1);

and an off-white color solid (0.5 g, $R_f$ 0.75 on silica gel TLC in 60% ethyl acetate in hexane) was isolated and characterized as 2-[Bis-(3-keto-5-methylfuranyl)]-3,5-di-tert-butyl-4-hydroxyphenylmethane(5), m.p. 178.3-180.6° C.;

$^1$H NMR (CDCl$_3$, 300 MHz): δ 1.396 (s, 18H), 2.145 (s, 6H), 3.469 (t, J=5.7 Hz, 6.3 Hz, 1H), 5.141 (s, 1H), 5.202 (d, J=6.3 Hz, 1H), 5.203 (d, J=6.0 Hz, 1H), 5.285 (s, 1H), 5.288 (s, 1H), 6.994 (s, 2H).

$^{13}$C NMR (CDCl$_3$, 75 MHz): δ 16.845, 30.326, 34.241, 47.817, 84.031, 105.084, 123.741, 125.603, 135.052, 153.240, 190.296, 203.257.

MS: m/e 413 (M$^+$+1).

Example VII

Differential Inhibitory Effects of Compounds Represented by Structures 4 (a-e) and 5 on Inducible Nitric Oxide Synthase RAW 264.7 cells, derived from murine macrophage (American Type Culture Collection, MD, USA) were cultured in DMEM supplemented with 10% endotoxin-free, heat-inactivated fetal calf serum, 100 units/mL penicillin and 100 mcg/mL streptomycin, the culture media was changed to serum-free DMEM without phenol red on reaching cell density 2-3×10$^6$ cells/mL, and the cells activated by incubation in medium containing E coli LPS (100 ng/mL). Test compounds dissolved in dimethylsulfoxide were added together with the LPS. Cells treated with 0.05% DMSO acted as vehicle control.

The effects of test compounds on LPS-induced iNOS (inducible nitric oxide synthase) and COX-2 protein expressions were studied by Western blotting. LPS treatment significantly increased iNOS and COX-2 protein levels, whereas co-treatment with inotilone (4a) suppressed the induction of iNOS but not of COX-2 in a concentration dependent manner. Methylinotilone (4b) showed slightly stimulated LPS-induced COX-2 expression, but no effect on LPS induced iNOS protein expression.

While iNOS induction can protect the brain from certain infectious diseases, excessive levels of nitric oxide (NO) are toxic to neurons (Licinio, J et al., Molecular Medicine Today, 5(5): 225-232(8)). Therefore compounds of the invention are potentially useful in preventing the progression of neurodegenerative disorders such as Alzhiemer's disease, dementia and Parkinson's disease.

Increased NO production via induction of iNOS has been suggested as a major mechanism by which cytokines mediate cardiac contractile dysfunction and development of cardiovascular disease. Increased expression of nitric oxide synthase isoforms is associated with human atherogenesis and the activity of the enzymes in an atherosclerotic environment may promote the formation of peroxynitrite (Perrotta, I et al. Cardiovasc Pathol. 2010 Jul. 7. [Epub ahead of print]). Therefore the compounds of the invention are potentially useful in preventing atherosclerosis.

Over-expression of iNOS, a common phenomenon during chronic inflammatory conditions, generates sustainable amounts of NO, and its reactive intermediates are mutagenic, causing DNA damage or impairment of DNA repair. Increased expression of iNOS has been involved in tumors of the colon, lung, oropharynx, reproductive organs, breast, and CNS (Central Nervous System) besides its occurrence in chronic inflammatory diseases (Lala, P K et al. Lancet Oncol. 2001 March; 2(3):149-56). Compounds of the invention that are selective inhibitors of iNOS are therefore potentially useful in preventing the onset of tumorigenesis, and in inhibiting the progression of various types of cancer.

The invention claimed is:

1. Compound of structure 4e represented by:

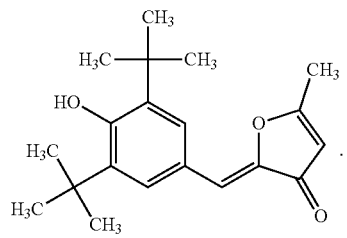

4e

2. A dietary supplement comprising the compounds of claim 1 formulated with pharmaceutically acceptable carriers.

3. A composition for topical use comprising the compounds of claim 1 formulated with pharmaceutically acceptable excipients.

* * * * *